United States Patent
Nishihara et al.

(10) Patent No.: US 9,145,430 B2
(45) Date of Patent: Sep. 29, 2015

(54) SEPARATING AGENT FOR CHROMATOGRAPHY

(75) Inventors: Keiji Nishihara, Himeji (JP); Junichi Ishii, Nagoya (JP)

(73) Assignee: DAICEL CORPORATION, Osaka-shi, Osaka (JP)

( * ) Notice: Subject to any disclaimer, the term of this patent is extended or adjusted under 35 U.S.C. 154(b) by 169 days.

(21) Appl. No.: 13/877,405

(22) PCT Filed: Oct. 12, 2011

(86) PCT No.: PCT/JP2011/073415
§ 371 (c)(1),
(2), (4) Date: Apr. 2, 2013

(87) PCT Pub. No.: WO2012/050124
PCT Pub. Date: Apr. 19, 2012

(65) Prior Publication Data
US 2013/0204014 A1    Aug. 8, 2013

(30) Foreign Application Priority Data
Oct. 13, 2010   (JP) .................................. 2010-230433

(51) Int. Cl.
C07D 321/00    (2006.01)
C07F 7/18      (2006.01)
(Continued)

(52) U.S. Cl.
CPC .................. C07F 7/18 (2013.01); B01J 20/289 (2013.01); B01J 20/29 (2013.01); B01J 20/3219 (2013.01);
(Continued)

(58) Field of Classification Search
CPC ....... C07D 323/00; C07F 7/18; C07F 7/1864; B01J 20/29; B01J 20/3253; B01J 20/3255; B01J 20/3219; B01J 20/3225; B01J 20/3272; B01J 20/289; C07B 57/00; C07B 2200/11
USPC ................................................. 549/214, 200
See application file for complete search history.

(56) References Cited

U.S. PATENT DOCUMENTS 4,842,935 A    6/1989   Shinbo et al.
4,942,149 A    7/1990   Shinbo et al.
(Continued)

FOREIGN PATENT DOCUMENTS

JP    62-210053    9/1987
JP    02-069472    3/1990
(Continued)

OTHER PUBLICATIONS

Notification of Transmittal of Translation of the International Preliminary Report on Patentability dated May 16, 2013 (7 pages).
Corresponding Chinese Office Action dated Jan. 30, 2014, including English translation (16 pages).
Corresponding Supplemental EPO Search Report dated Mar. 3, 2014 (15 pages).
(Continued)

*Primary Examiner* — T. Victor Oh
(74) *Attorney, Agent, or Firm* — Flynn, Thiel, Boutell & Tanis, P.C.

(57) ABSTRACT

A separating agent for chromatography is provided that is useful for the separation of specific compounds, e.g., for the optical resolution of amino acids. This separating agent for chromatography provides a higher productivity and contains a crown ether-like cyclic structure and optically active binaphthyl. This separating agent for chromatography containing a crown ether-like cyclic structure and optically active binaphthyl is provided by introducing a substitution group for binding to a carrier into a specific commercially available 1,1'-binaphthyl derivative that has substituents at the 2, 2', 3, and 3' positions, then introducing a crown ether-like cyclic structure, and subsequently chemically bonding the binaphthyl derivative to the carrier through the substitution group for binding to the carrier.

11 Claims, 4 Drawing Sheets

(51) Int. Cl.

| | |
|---|---|
| *C07D 323/00* | (2006.01) |
| *B01J 20/29* | (2006.01) |
| *B01J 20/32* | (2006.01) |
| *B01J 20/289* | (2006.01) |
| *C07B 57/00* | (2006.01) |

(52) U.S. Cl.
CPC .......... *B01J 20/3225* (2013.01); *B01J 20/3253* (2013.01); *B01J 20/3255* (2013.01); *B01J 20/3272* (2013.01); *C07B 57/00* (2013.01); *C07D 323/00* (2013.01); *C07F 7/1864* (2013.01); *C07B 2200/11* (2013.01)

(56) References Cited

U.S. PATENT DOCUMENTS

| | | |
|---|---|---|
| 2002/0019491 A1 | 2/2002 | Bruening et al. |
| 2004/0132998 A1 | 7/2004 | Bruening et al. |

FOREIGN PATENT DOCUMENTS

| | | |
|---|---|---|
| JP | 02-290898 | 11/1990 |
| JP | 03-057816 | 3/1991 |
| JP | 03-106852 A | 5/1991 |
| JP | 2003-535819 | 12/2003 |
| KR | 2002-0020440 A | 3/2002 |
| KR | 2004-0080034 | 9/2004 |
| WO | WO 2009/023452 A1 | 2/2009 |

OTHER PUBLICATIONS

Database WPI, Week 200267, Thomson Scientific, London, GB; AN 2002-624445, XP-002720293 (1 page).

"Enantiomer separation of amino compounds by a novel chiral stationary phase derived from crown ether", by Y. Machida et al, Journal of Chromatography A, vol. 805, 1998, pp. 85-92.

"Preparation and chiral recognition of (S)-binaphthol derivative-bonded phase for high-performance liquid chromatography", by Y. Sudo et al, Journal of Chromatography A, vol. 813, 1998, pp. 35-45.

"Liquid chromatographic resolution of β-amino acids on CSPs, based on optically active (3,3'-diphenyl-1,1'-binaphthyl)-20-crown-6", by H. Choi et al, Analytica Chimica Acta, vol. 619, 2008, pp. 122-128.

International Search Report of PCT/JP2011/073415 (2 pgs.).

New chiral crown ether stationary phase for the liquid chromatographic resolution of α-amino acid enantiomers, by Myung Ho Hyun et al, Journal of Chromatography A, vol. 910, 2001, pp. 359-365.

Effect of the residual silanol group protection on the liquid chromatographic resolution of racemic primary amino compounds on a chiral stationary phase based on optically active (3,3'-diphenyl-1,1'-binaphthyl)-20-crown-6, by Myung Ho Hyun, Journal of Chromatography A, vol. 1138, 2007, pp. 169-174.

Chinese Office Action and Search Report dated Oct. 10, 2014, with English translation (19 pages).

*Improved crown ether-based chiral stationary phase*, by T. Shinbo et al, Journal of Chromatography, vol. 625, 1992, pp. 101-108.

SEPARATING AGENT FOR CHROMATOGRAPHY

TECHNICAL FIELD

The present invention relates to a separating agent for chromatography and relates to a separating agent for chromatography that contains a crown ether-like cyclic structure and optically active binaphthyl.

BACKGROUND ART

Various separating agents having various specific structures adapted to the compounds to be separated are known as separating agents for chromatography. The following, for example, are known for these specific structures: crown ether-like cyclic structures, binaphthyl structures, phenyl ester structures, and phenyl carbamate structures.

Within the sphere of separating agents for chromatography that contain a crown ether-like cyclic structure and a binaphthyl structure, a separating agent for optical isomers is known in which a binaphthyl derivative having a crown ether-like cyclic structure bridging across the individual naphthyl rings in the binaphthyl is adsorbed on a carrier (refer, for example, to Patent Document 1). This separating agent for optical isomers is suitable for the optical resolution of compounds that have an amino group, e.g., amino acids.

In addition, as separating agents for chromatography in which the aforementioned binaphthyl derivative is supported by chemical bonding to a carrier, separating agents for chromatography in which the binaphthyl structure or the crown ether-like structure of a binaphthyl derivative with formula (i) or (ii) below is bonded by chemical bonding to the surface of a carrier, for example, are known (refer, for example, to Nonpatent Documents 1 and 2 and Patent Document 2). The separating agent for chromatography containing the binaphthyl derivative with formula (i) is known to have the optical resolving power with respect to amino acids, while the separating agent for chromatography containing the binaphthyl derivative with formula (ii) is known to lack the optical resolving power with respect to amino acids. Furthermore, with regard to the separating agent for chromatography that contains the binaphthyl derivative with formula (i), art is also known in which the residual silanol groups in the silica gel used as the carrier are protected by treatment using n-octyltriethoxysilane (for example, Nonpatent Document 2), and the optical resolving power with respect to α-amino acids, amines, and amino alcohols is known to be improved by this treatment.

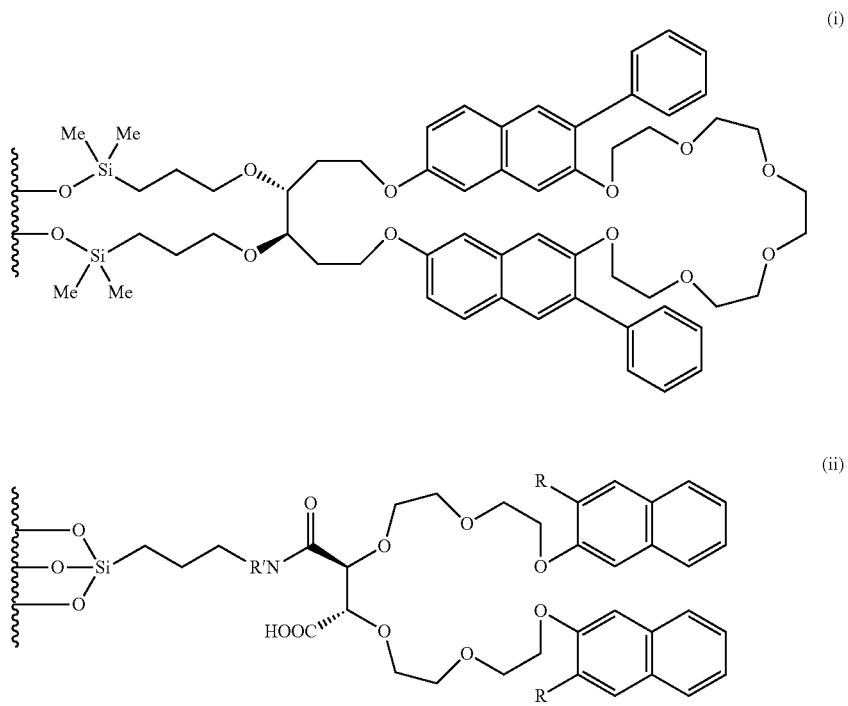

The binaphthyl derivative with formula (i) has promise as a separating agent effective for the optical resolution of amino acids and, while it can be synthesized using commercially available products as the starting materials, the synthesis route is lengthy and there remains room for investigation from a productivity perspective.

CITATION LIST

Patent Document

Patent Document 1 Japanese Examined Patent Publication No. H3-57816
Patent Document 2 Korean Patent Application Publication No. 20040080034

Non-Patent Document

Non-patent Document 1 *J. Chromatogra. A*, 910 (2001) 359
Non-patent Document 2 *J. Chromatogra. A*, 1138 (2007) 169

SUMMARY OF INVENTION

Technical Problems

The present invention provides a separating agent for chromatography that contains a crown ether-like cyclic structure and optically active binaphthyl, that is useful for the separation of specific compounds, e.g., for the optical resolution of amino acids, and that provides a higher productivity.

Solution to Problem

The present inventors discovered that a separating agent for chromatography containing a crown ether-like cyclic structure and optically active binaphthyl can be more easily obtained by introducing a substitution group for binding to carrier that will bond to the carrier into a binaphthyl derivative, then introducing a crown ether-like cyclic structure into the binaphthyl derivative, and chemically bonding the resulting binaphthyl derivative to the carrier. The present invention was achieved based on this discovery.

Thus, the present invention provides a separating agent for chromatography, having a carrier and an optically active binaphthyl compound bonded by chemical bonding to the surface of the carrier, wherein the binaphthyl compound is represented by the following formula (I).

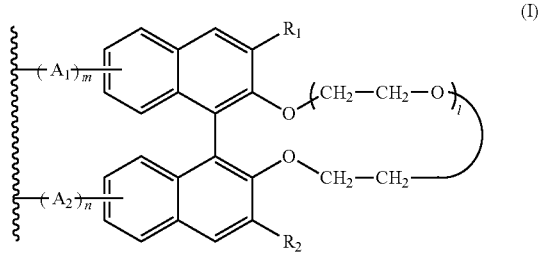

In formula (I), $R_1$ and $R_2$ each represent hydrogen, a possibly substituted phenyl group, a possibly substituted naphthyl group, a possibly substituted $C_{1-8}$ alkyl group in which any noncontiguous methylene group may be oxygen, or a trialkylsilyl group in which the number of carbons in each alkyl group is 1 or 2; $A_1$ and $A_2$ each represent a group that is bonded to the surface of the carrier and that is substituted for hydrogen on a binaphthyl ring; and l represents an integer from 4 to 6, and m and n each represent an integer from 0 to 5 wherein m+n is from 1 to 10.

The present invention further provides the aforementioned separating agent for chromatography wherein l is 4; the aforementioned separating agent for chromatography wherein $R_1$ and $R_2$ are the phenyl group; the aforementioned separating agent for chromatography wherein $A_1$ and $A_2$ each contain a structure represented by the following formula (II) that is substituted for hydrogen in the binaphthyl with formula (I); the aforementioned separating agent for chromatography wherein one of m and n is 1 and the other is 0; and the aforementioned separating agent for chromatography wherein the surface of the carrier exhibits hydrophobicity.

In formula (II), o represents an integer from 1 to 30.

The present invention further provides a method of producing a separating agent for chromatography, including: a step B of introducing a substitution group for binding to a carrier into a binaphthyl ring of a binaphthyl derivative A represented by the following formula (III), to obtain a binaphthyl derivative B; a step C of hydrolyzing methoxy groups at positions 2 and 2' of the binaphthyl derivative B to obtain a binaphthyl derivative C in which the methoxy groups have been converted into hydroxyl groups; a step D of crosslinking both of the hydroxyl groups in the binaphthyl derivative C with a polyethylene glycol derivative to obtain a binaphthyl derivative D having a crown ether-like cyclic structure; and a step E of bonding the binaphthyl derivative D to the surface of the carrier through the substitution group for binding to carrier on the binaphthyl derivative D by chemical bonding.

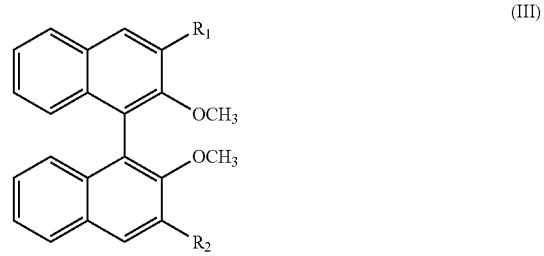

In formula (III), $R_1$ and $R_2$ are the same as the $R_1$ and $R_2$ in formula (I), respectively.

The present invention also provides the aforementioned production method further including a step A of substituting bromo groups in 3,3'-dibromo-2,2'-dimethoxy-1,1'-binaphthyl with $R_1$ and $R_2$, respectively, to obtain the binaphthyl derivative A.

The present invention also provides the aforementioned production method wherein the binaphthyl derivative B is obtained in step B by reacting the binaphthyl derivative A with $C_{4-33}$ aliphatic dicarboxylic acid monomethyl ester monochloride in the presence of iron chloride.

The present invention also provides the aforementioned production method wherein the binaphthyl derivative D is obtained in step D by crosslinking the hydroxyl groups in the binaphthyl derivative C by the reaction, under alkaline conditions, of polyoxyethylene glycol ditosylate having from 5 to 7 repetitions of an oxyethylene group.

The present invention also provides the aforementioned production method wherein in step E, a surface-treated silica gel is used for the carrier and chemical bonding is effected between the substitution group for binding to the carrier in the binaphthyl derivative D and a functional group provided by the surface treatment of the silica gel.

The present invention also provides the aforementioned production method further including a step F of hydrophobing hydrophilic groups on the surface of the carrier.

Advantageous Effects of Invention

Because the binaphthyl derivative in the separating agent for chromatography of the present invention has a structure that enables the introduction first of a substitution group for binding to a carrier and then a crown ether-like cyclic structure in this sequence into a binaphthyl derivative having methoxy groups at positions 2 and 2' of the binaphthyl ring, a separating agent for chromatography can be provided that contains a crown ether-like cyclic structure and optically active binaphthyl, that is useful, for example, for the optical resolution of amino acids, and that provides a higher productivity.

DESCRIPTION OF EMBODIMENTS

Figure 1:
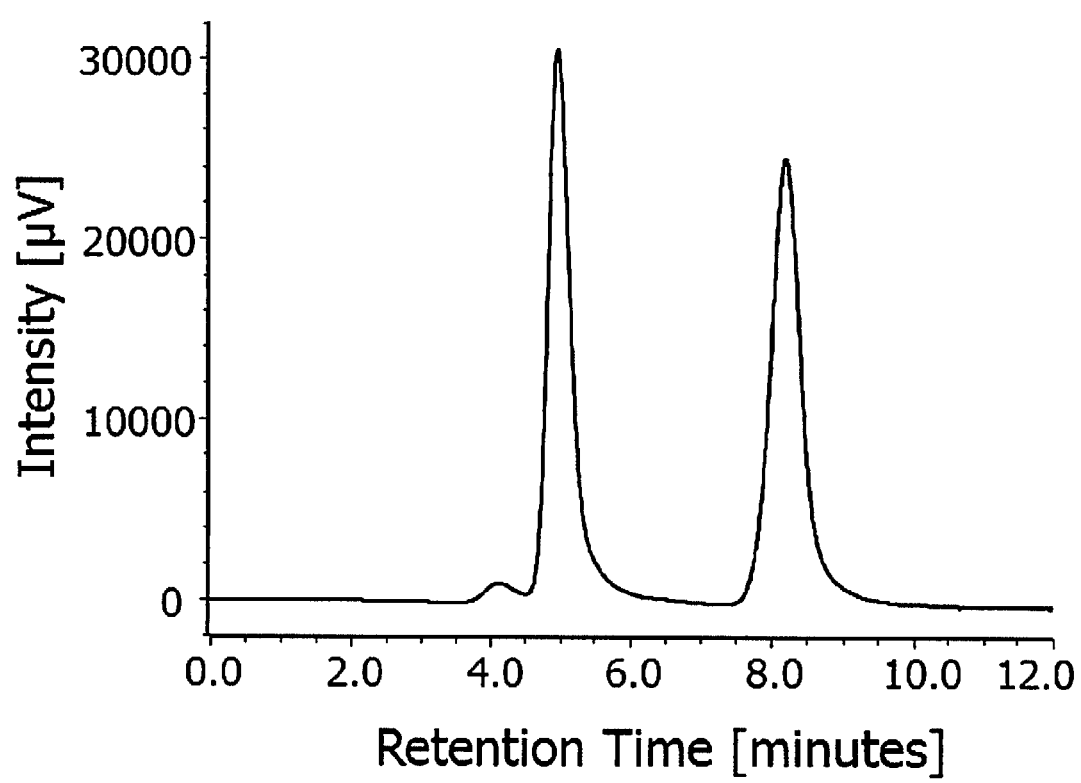
FIG. 1 is a diagram that shows a chromatogram for the optical resolution of alanine using the column 4 of the present invention.
Figure 2:
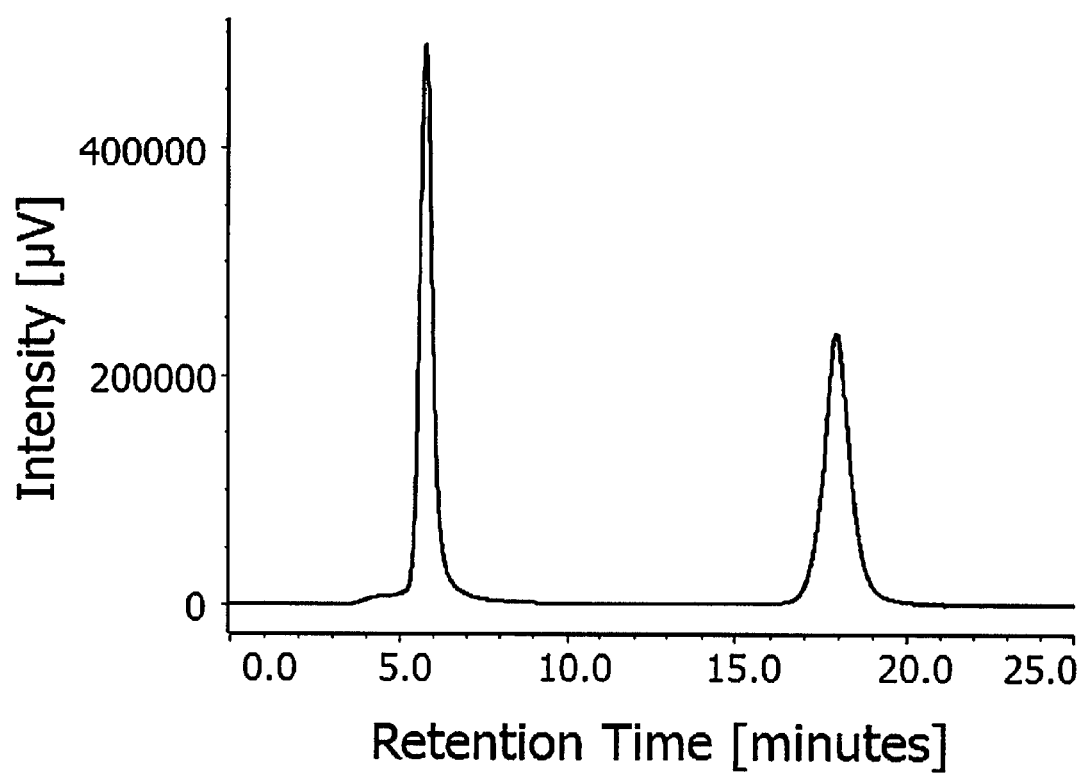
FIG. 2 is a diagram that shows a chromatogram for the optical resolution of methionine using the column 4 of the present invention.
Figure 3:
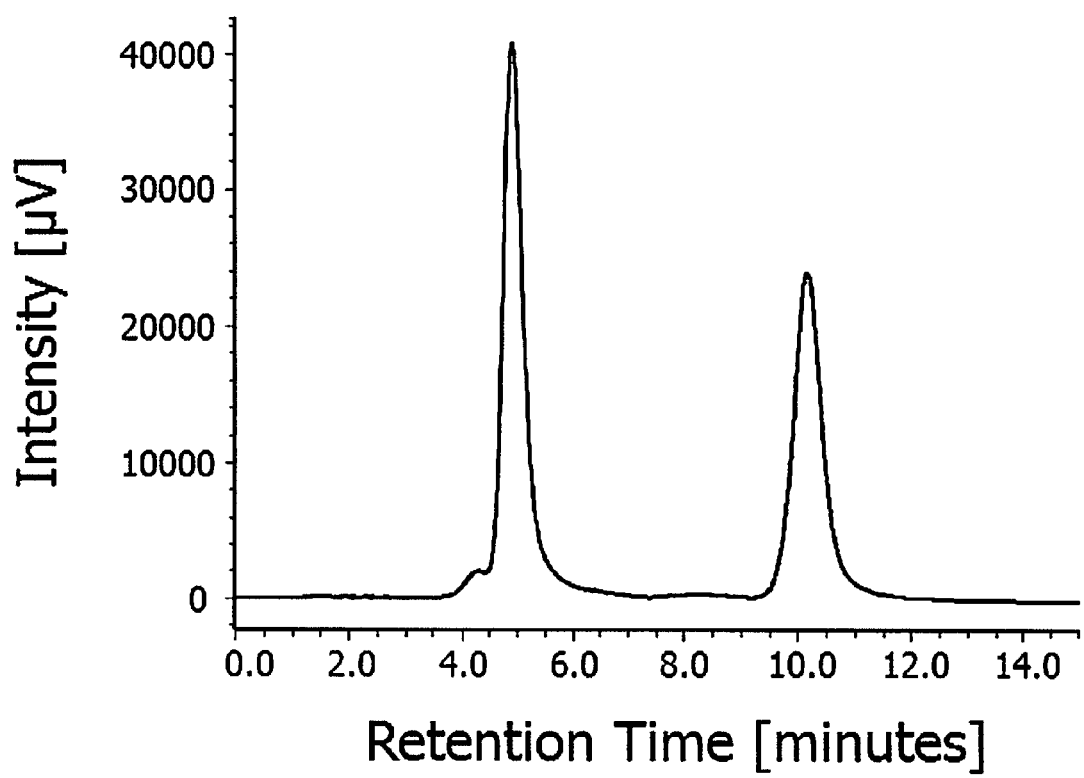
FIG. 3 is a diagram that shows a chromatogram for the optical resolution of glutamic acid using the column 4 of the present invention.
Figure 4:
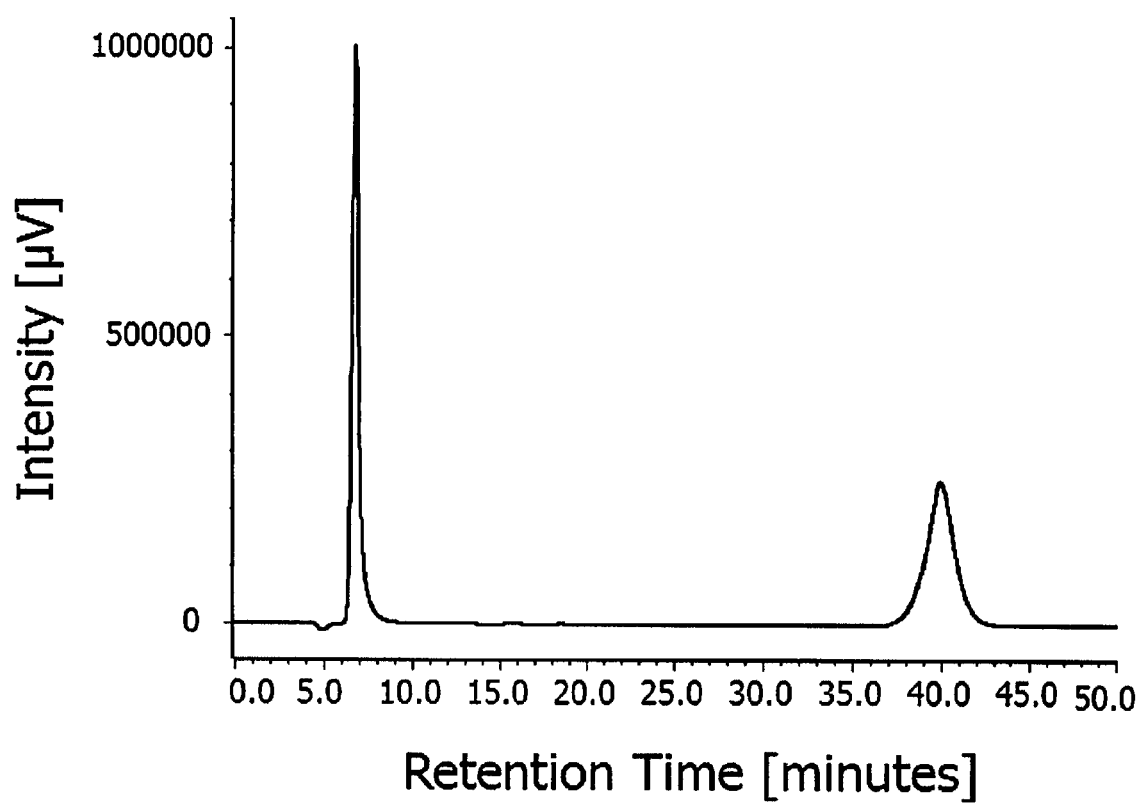
FIG. 4 is a diagram that shows a chromatogram for the optical resolution of phenylglycine using the column 4 of the present invention.

The separating agent for chromatography of the present invention comprises a carrier and an optically active binaphthyl compound that is bonded by chemical bonding to the surface of the carrier. This binaphthyl compound is given by formula (I) below. This binaphthyl compound is the S-isomer or R-isomer, but may also be a mixture of the S- and R-isomers within a range in which the optical resolving power is exhibited. This binaphthyl compound is ordinarily a single species, but also encompasses two or more species having different values for m and/or n.

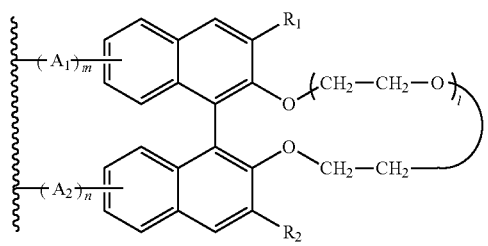

$R_1$ and $R_2$ in formula (I) each represent hydrogen, a possibly substituted phenyl group, a possibly substituted naphthyl group, a possibly substituted $C_{1-8}$ alkyl group in which any noncontiguous methylene group may be oxygen, or a trialkylsilyl group in which the number of carbons in each alkyl group is 1 or 2. The substituent that may be present on the phenyl group and so forth in $R_1$ and $R_2$ is a group that does not interact with the oxygen atoms in the crown ether-like cyclic structure, and such a substituent can be exemplified by the methyl group and chloro group. Viewed from the perspective of improving the separation performance, $R_1$ and $R_2$ are preferably both a phenyl group.

$A_1$ and $A_2$ in formula (I) each represent a group that is bonded to the surface of the carrier and that is substituted for hydrogen on the binaphthyl ring. The size of $A_1$ and $A_2$ is not particularly limited; however, viewed from the standpoints of the ease of synthesis and improving the separation performance, the molecular weight of each is preferably from 100 to 600. $A_1$ and $A_2$ can be constructed from a variety of groups, for example, $C_{1-30}$ alkylene groups, $C_{6-30}$ arylene groups, an ether group, a carbonyl group, an imino group, an amide group, and so forth.

Viewed from the standpoint of ease of synthesis of the above-described binaphthyl compound, $A_1$ and $A_2$ preferably each contain the structure represented by the following formula (II) substituted for hydrogen in the binaphthyl with formula (I).

In formula (II), o represents an integer from 1 to 30. Considered from the standpoints of ease of synthesis and boosting the separation performance, o is preferably from 4 to 10.

In formula (I), l represents an integer from 4 to 6. This l is more preferably 4 from the standpoint of inclusion of the ammonium ion.

In formula (I), m and n each represent an integer from 0 to 5. However, m+n is from 1 to 10. m and n are preferably both at least 1 from the standpoint of the ease of synthesis of the binaphthyl compound while, more preferably, one of m and n is 1 and the other is 0. When m or n is 0, this means that there is no bond with the carrier.

A carrier that can immobilize the binaphthyl compound by chemical bonding can be used for the carrier under consideration. This carrier may be an inorganic carrier or an organic carrier. The inorganic carriers can be exemplified by silica, alumina, magnesia, glass, kaolin, titanium oxide, a silicic acid salt, and hydroxyapatite. The organic carriers can be exemplified by polystyrene, polyacrylamide, and polyacrylate.

The carrier can be used in a form adapted to the particular type of chromatography. The carrier form can be exemplified by particulate and by a porous cylinder housed in a liquid-tight manner in a columnar tube.

Viewed from the standpoint of boosting the separation performance, the carrier is preferably porous and more preferably has a BET specific surface area of from 100 to 600 $m^2/g$. With regard to the pore diameter of a porous carrier, the pore diameter, as measured by mercury porosimetry, is preferably from 60 to 300 angstroms viewed from the standpoint of boosting the separation performance.

For example, silica gel is a particularly preferred carrier considering the properties referenced above.

Viewed from the standpoint of the ease of synthesis of the binaphthyl compound, the carrier is preferably subjected to a surface treatment with a surface treatment agent in order to form on the carrier surface a functional group that will constitute a portion of the $A_1$ and/or $A_2$ in formula (I). This surface treatment agent can be selected as appropriate in conformity with the type of carrier.

When, for example, the carrier is a silica gel, a silane coupling agent can be used for the surface treatment agent. This silane coupling agent can be exemplified by 3-aminopropyltriethoxysilane and 3-(2-aminoethylaminopropyl)trimethoxysilane.

Viewed from the standpoint of boosting the separation performance, the surface of the carrier preferably exhibits hydrophobicity. Such a carrier can be exemplified by a carrier whose surface has been treated with a hydrophobic group.

The separating agent for chromatography of the present invention is used processed as appropriate in conformity with the type of chromatography. For example, in the case of use for column chromatography, the separating agent for chromatography of the present invention is packed or housed in a columnar tube. In the case of use for thin-layer chromatography, the separating agent for chromatography of the present invention, when used as, for example, a particulate separating agent, is used formed into a thin layer on the surface of a substrate, e.g., a glass plate or a plastic plate. This processing can be carried out by ordinary methods.

Regardless of the optical properties of the binaphthyl compound, the separating agent for chromatography of the present invention can be used for the separation of specific compounds other than optical isomers, but which interact with the structure of the binaphthyl compound. When used for such a separation of compounds other than optical isomers, the binaphthyl compound may even be a mixture of the S- and R-isomers to the extent that the optical resolving power is not exhibited (for example, it may be the racemic body).

The separating agent for chromatography of the present invention can be produced by a method comprising a step B of introducing a substitution group for binding to a carrier into the binaphthyl ring of a binaphthyl derivative A represented by formula (III) below, to obtain a binaphthyl derivative B; a step C of hydrolyzing the methoxy groups at positions 2 and 2' of the binaphthyl derivative B to obtain a binaphthyl derivative C in which these methoxy groups have been converted into hydroxyl groups; a step D of crosslinking both of the hydroxyl groups in the binaphthyl derivative C with a polyethylene glycol derivative to obtain a binaphthyl derivative D having a crown ether-like cyclic structure; and a step E of bonding the binaphthyl derivative D to the surface of the carrier through the substitution group for binding to carrier on the binaphthyl derivative D by chemical bonding.

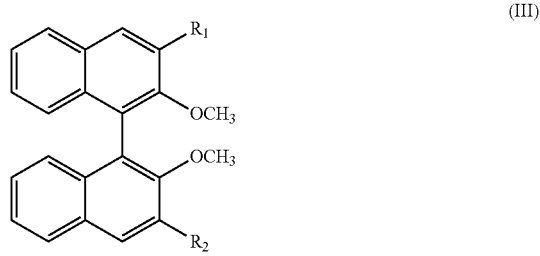

(III)

$R_1$ and $R_2$ in formula (III) are the same as $R_1$ and $R_2$ in formula (I). The binaphthyl derivative A can be acquired as a commercially available product. Such a commercially available product can be exemplified by 2,2'-dimethoxy-1,1'-binaphthyl and 3,3'-dibromo-2,2'-dimethoxy-1, 1'-binaphthyl (both products of Tokyo Chemical Industry Co., Ltd.). The use of such commercially available products is preferred from the standpoint of the ease of synthesis of the binaphthyl compound.

The binaphthyl derivative A can also be acquired by synthesis. For example, the binaphthyl derivative A can be obtained by synthesis from 3,3'-dibromo-2,2'-dimethoxy-1, 1'-binaphthyl. Viewed in terms of generating variety for the $R_1$ and $R_2$ in the binaphthyl compound, such a method of the present invention preferably further comprises a step A of substituting the bromo groups in 3,3'-dibromo-2,2'-dimethoxy-1,1'-binaphthyl with $R_1$ and $R_2$, respectively, to obtain the binaphthyl derivative A.

The substitution group for binding to carrier referenced in step B may be a group that bonds with a functional group on the carrier surface or may be a group that directly bonds to the surface of the carrier. The substitution group for binding to carrier may be a single species or two or more species. At least one substitution group for binding to carrier may be present or two or more may be present. When there are two or more substitution groups for binding to carrier, the substitution groups for binding to the carrier may be bonded to only one of the two naphthyl rings in the binaphthyl or may be bonded to both. Viewed from the perspective of the ease of bonding between the binaphthyl derivative D and the carrier, the substitution group for binding to the carrier is preferably a group that bonds to a functional group provided by surface treatment of the carrier.

An example of a preferred step B is a step in which the binaphthyl derivative B is obtained by reacting the binaphthyl derivative A with a $C_{4-33}$ aliphatic dicarboxylic acid monomethyl ester monochloride in the presence of iron chloride.

Given that the 2 and 2' positions of the binaphthyl also have a high reactivity in the binaphthyl derivative B, step C can be carried out by reaction under moderate temperature conditions. These reaction conditions can be exemplified by a boron tribromide-mediated dealkylation reaction at room temperature or in an ice bath. The execution of step C under such conditions is preferred because this restrains the effects on the other structures in the binaphthyl derivative B and provides the binaphthyl derivative C in better yields.

The step D can be carried out using conditions that induce crosslinking by polyoxyethylene across the hydroxyl groups at the 2 and 2' positions of the binaphthyl derivative C. This crosslinking can be carried out utilizing hydrolysis: for example, it can be carried out by a reaction, under alkaline conditions, of polyoxyethylene glycol ditosylate having from 5 to 7 repetitions of the oxyethylene group.

The step E can be carried out as appropriate using a class of known art in conformity to the type of the substitution group for binding to carrier and the type of carrier. For example, when a surface-treated silica gel is used for the carrier, step E can be carried out by bringing about chemical bonding between the substitution group for binding to carrier in the binaphthyl derivative D and a functional group that has resulted from the surface treatment of the silica gel. This chemical bonding can be effected by carrying out a reaction using a coupling agent such as, for example, 1-ethyl-3-(3-dimethylaminopropyl)carbodiimide hydrochloride (WSC), O-(7-azabenzotriazol-1-yl)-N,N,N',N'-tetramethyluronium hexafluorophosphate (HATU), 1H-benzotriazol-1-yloxytripyrrolidinophosphonium hexafluorophosphate (PyBop), or 4-(4,6-dimethoxy-1,3,5-triazin-2-yl)-4-methylmorpholinium chloride.nH$_2$O (DMT-MM).

The binaphthyl derivative obtained in each particular step may be purified or the product may be used as such as the starting material in the ensuing step.

The present invention may further comprise a step F of hydrophobing the hydrophilic groups on the surface of the carrier. The step F is preferably carried out after step E. The step F can be carried out by the action, on the carrier or the product of step E, of a surface treatment agent having a hydrophobic organic group or a hydrophobing agent that reacts with a hydrophilic group on the carrier surface to form a hydrophobic group. The hydrophilic group on the carrier surface can be exemplified by, for example, hydroxyl groups and/or amino groups that are present on the surface of the carrier, e.g., silica gel, and/or on the carrier surface after the above-described surface treatment.

The surface treatment agent having a hydrophobic organic group can be exemplified by hexamethyldisilazane, n-octadecyltriethoxysilane, and n-octadecyltrimethoxysilane. The hydrophobing agent referenced above can be selected as appropriate in conformity to the type of hydrophilic group and can be exemplified for the case of the amino group by acetic anhydride, decanoic acid, and stearic acid. The hydrophobic group formed on the carrier surface by the step F is preferably constructed with the same or similar structure and on the same scale as the $(A_1)_m$ and $(A_2)_n$ described above.

According to the method of the present invention, the reaction in each individual step is a one-stage reaction and, excluding the step F, the separating agent for chromatography of the present invention can be obtained in a four-stage reaction when the synthesis of the binaphthyl derivative A is not included and in a five-stage reaction when the step A of synthesizing the binaphthyl derivative A is included.

Examples

Synthesis of Chiral Crown Ether (1)

Operating under a nitrogen atmosphere, 0.946 g (S)-3,3'-dibromo-2,2'-dimethoxy-1,1'-binaphthyl, 0.736 g phenylboronic acid, and 24.8 mg tetrakis(triphenylphosphine)palladium $(Pd(PPh_3)_4)$ were dissolved in 20 mL toluene. To this was added 7 mL of a saturated aqueous solution of potassium carbonate and heating was carried out for 4 hours at 100° C. This was followed by washing of the reaction solution with saturated aqueous sodium chloride and extraction with ethyl acetate. The obtained organic phase was dried over anhydrous $MgSO_4$ and concentrated to obtain a crude product, which was purified by silica gel column chromatography to obtain the dimethyl ether (1-1) given by the following structural formula.

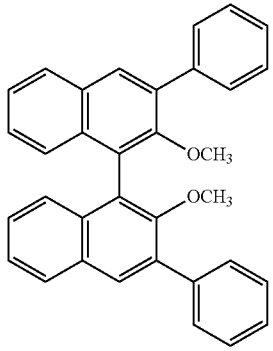
(1-1)

537 mg methyl adipoyl chloride was dissolved in 6 mL dichloromethane and 411 mg iron(III) chloride was then added and stirring was performed for 1 hour at room temperature. This solution was added dropwise to 466 mg of the compound of formula (1-1) dissolved in 15 mL dichloromethane and stirring for 24 hours at room temperature was then performed. This was followed by the addition of a saturated aqueous sodium bicarbonate solution and ethyl acetate and stirring at room temperature and then separation. The obtained organic phase was washed with saturated aqueous sodium chloride, dried over anhydrous $MgSO_4$, and concentrated to obtain a crude product, which was purified by silica gel column chromatography to obtain the acylated product (1-2) given by the following structural formula.

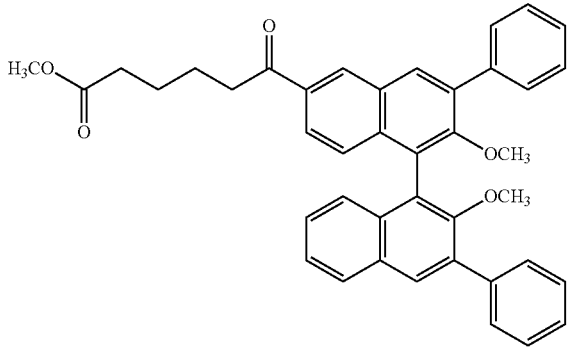
(1-2)

599 mg of the compound of formula (1-2) was dissolved in 25 mL dichloromethane; 12 mL of a 1 M dichloromethane solution of $BBr_3$ was added dropwise in an ice bath; and stirring was performed for 1 hour at room temperature. After this, 10 mL methanol was added dropwise; the solution was concentrated under a reduced pressure; extraction with ethyl acetate was performed; the obtained organic phase was washed with saturated aqueous sodium chloride, dried over anhydrous $MgSO_4$, and concentrated to provide a crude product; and the crude product was purified by silica gel column chromatography to obtain the binaphthyl (1-3) given by the following structural formula.

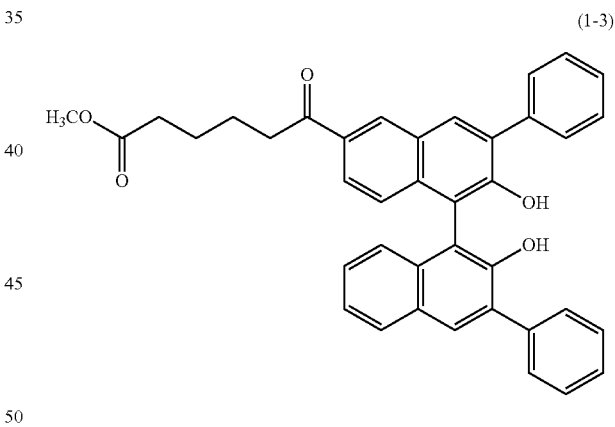
(1-3)

53.2 mg potassium hydroxide was added to 100 mg of the compound of formula (1-3) followed by the addition of 111 mg pentaethylene glycol ditosylate dissolved in 10 mL tetrahydrofuran and stirring for 4 hours at 80° C. After this, 2 mL of a 10% aqueous sodium hydroxide solution and 10 mL methanol were added at room temperature; stirring was performed for 30 minutes at room temperature; neutralization was then carried out with 2N hydrochloric acid; the solution was concentrated under a reduced pressure and extracted with ethyl acetate; the obtained organic phase was dried over anhydrous $MgSO_4$ and concentrated and the obtained crude product was purified by silica gel column chromatography to obtain the chiral crown ether (1) represented by the following structural formula.

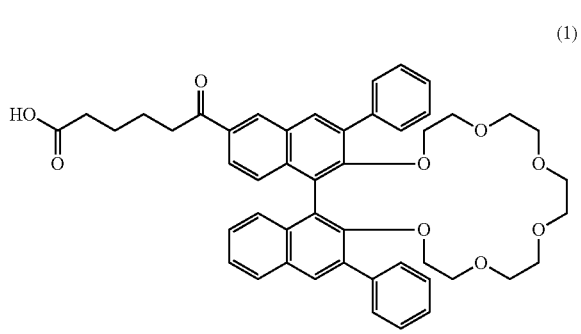 [SMILES: O=C(O)CCCCC(=O)c1ccc2c3c(c(-c4ccccc4)cc2c1)OCCOCCOCCOCCOCCOc1c(-c2ccccc2)cc2ccccc2c1-3]

(1)

Synthesis of Solid Phase (1)

508 mg of the synthesized chiral crown ether of formula (1), 156 mg 1-ethyl-3-(3-dimethylaminopropyl)carbodiimide hydrochloride (WSC), 123 mg 1-hydroxy-1H-benzotriazole monohydrate (HOBt), and 3.31 g 3-aminopropyl silica gel (average particle diameter=5 μm, average pore diameter=120 angstroms, surface area=330 m²/g) were dissolved in 66 mL N,N'-dimethylformamide (DMF) and stirring was performed for 24 hours at room temperature. Then, the solids obtained by filtration were successively washed three times with 20 mL each of DMF, dilute hydrochloric acid/methanol solution, and methanol, and dried. 2.00 g of the obtained solids and 61.3 mg 4-dimethylaminopyridine were dissolved in 10 mL dichloromethane; to this was added 567 mg acetic anhydride dissolved in 10 mL dichloromethane; and stirring was carried out for 5 hours at room temperature. The solids obtained by filtration were then successively washed two times with 20 mL each of dichloromethane and methanol and dried to obtain a solid phase (1) according to the present invention. It was calculated from the results of elemental analysis that approximately 0.083 mmol of the chiral crown ether of formula (1) was bonded per 1 g of the solid phase.

Synthesis of Solid Phase (2)

1.29 g 3-aminopropyl silica gel (average particle diameter=5 μm, average pore diameter=120 angstroms, surface area=330 m²/g) was dissolved in 10 mL DMF and 462 mg of the synthesized chiral crown ether (1), 342 mg O-(7-azabenzotriazol-1-yl)-N,N,N',N'-tetramethyluronium hexafluorophosphate (HATU), and 99.5 mg N-methylmorpholine dissolved in 15 mL DMF were added and stirring was performed for 24 hours at room temperature. Then, the solids obtained by filtration were successively washed three times with 25 mL each of DMF, dilute hydrochloric acid/methanol solution, and methanol, then an additional three times with 25 mL DMF (70° C., 1 hour), and then three times with 25 mL methanol (50° C., 1 hour) and dried to obtain solid phase (2). It was calculated from the results of elemental analysis that approximately 0.30 mmol of the chiral crown ether of formula (1) was bonded per 1 g of the solid phase.

Synthesis of Solid Phase (3)

602 mg of solid phase (2) was dissolved in 24 mL dried toluene; 1.0 mL 1,1,1,3,3,3-hexamethyldisilazane was added; and stirring was carried out for 6 hours at 136° C. The solids obtained by filtration were then successively washed three times with 15 mL each of toluene, ethyl acetate, and methanol and dried to obtain solid phase (3).

Synthesis of Solid Phase (4)

593 mg of solid phase (2) was dissolved in 5 mL DMF; 55.1 mg acetic acid, 245 mg HATU, and 68.4 mg N-methylmorpholine dissolved in 5 mL DMF were added; and stirring was performed for 24 hours at room temperature. Then, the solids obtained by filtration were successively washed three times with 15 mL each of DMF, dilute hydrochloric acid/methanol solution, and methanol, then an additional three times with 15 mL DMF (70° C., 1 hour), and then three times with 15 mL methanol (50° C., 1 hour) and dried to obtain solid phase (4).

Synthesis of Solid Phase (5)

552 mg of solid phase (2) was dissolved in 5 mL DMF; 69.0 mg decanoic acid, 228 mg HATU, and 62.2 mg N-methylmorpholine dissolved in 5 mL DMF were added; and stirring was performed for 24 hours at room temperature. Then, the solids obtained by filtration were successively washed three times with 15 mL each of DMF, dilute hydrochloric acid/methanol solution, and methanol and dried to obtain solid phase (5).

Synthesis of Solid Phase (6)

553 mg of solid phase (2) was dissolved in 5 mL DMF; 114 mg stearic acid, 228 mg HATU, and 69.2 mg N-methylmorpholine dissolved in 5 mL DMF were added; and stirring was performed for 24 hours at room temperature. Then, the solids obtained by filtration were successively washed three times with 15 mL each of DMF, dilute hydrochloric acid/methanol solution, and methanol and dried to obtain solid phase (6).

Production of Columns (1) to (6)

Using a slurry packing method, columns (1) to (6) were obtained by packing solid phases (1) to (6) in columnar tubes having an inner diameter of 2.1 mm and a length of 15 cm.

Evaluations

The sample was dissolved in each of the moving phases used in the measurements to provide a solution with a sample concentration of approximately 1 mg/1 mL and was analyzed by HPLC under the conditions indicated below and the retention factor, separation factor, and separation degree were determined. The results are given in Tables 1 to 6.

(Conditions)

A-1: aqueous perchloric acid solution (pH 1.5), 25° C.
A-2: aqueous perchloric acid solution (pH 1.5), 0° C.
B-1: aqueous perchloric acid solution (pH 1.5)/methanol=80/20 (v/v), 25° C.
B-2: aqueous perchloric acid solution (pH 1.5)/methanol=70/30 (v/v), 25° C.
B-3: aqueous perchloric acid solution (pH 1.5)/methanol=60/40 (v/v), 25° C.
B-4: aqueous perchloric acid solution (pH 1.5)/methanol=50/50 (v/v), 25° C.
B-5: aqueous perchloric acid solution (pH 1.5)/methanol=80/20 (v/v), 0° C.
C-1: aqueous perchloric acid solution (pH 1.5)/acetonitrile=95/5 (v/v), 25° C.
C-2: aqueous perchloric acid solution (pH 1.5)/acetonitrile=90/10 (v/v), 25° C.
C-3: aqueous perchloric acid solution (pH 1.5)/acetonitrile=80/20 (v/v), 25° C.
C-4: aqueous perchloric acid solution (pH 1.5)/acetonitrile=70/30 (v/v), 25° C.
C-5: aqueous perchloric acid solution (pH 1.5)/acetonitrile=90/10 (v/v), 0° C.
C-6: aqueous perchloric acid solution (pH 1.5)/acetonitrile=80/20 (v/v), 0° C.
D: hexane/ethanol/trifluoroacetic acid/water=50/50/0.5/0.5 (v/v), 25° C.

The retention factor, separation factor, and separation degree in the following tables are each defined as follows.

Math. 1 retention factor={(retention time of the enantiomer)−(dead time)}/dead time

The dead time for Tables 1 to 5 was measured using sodium oxalate and for Table 6 was measured using 1,3,5-tri-tertiary-butylbenzene (ttb).

Math. 2

$$\text{separation factor} = \text{retention factor of the more strongly absorbed enantiomer}/\text{retention factor of the more weakly absorbed enantiomer}$$

Math. 3

$$\text{separation degree} = 2 \times (\text{distance between the two peaks for the more strongly absorbed enantiomer and the more weakly absorbed enantiomer})/\text{sum of the band widths of the two peaks}$$

TABLE 1

Optical resolution with column 1

| sample | conditions | retention factor first peak | second peak | separation factor | separation degree |
|---|---|---|---|---|---|
| tryptophan | A-1 | 1.05 | 1.30 | 1.24 | 1.30 |
| phenylalanine | A-1 | 0.36 | 0.47 | 1.31 | — |
| leucine | A-1 | 0.15 | 0.28 | 1.87 | — |
| tryptophan | A-2 | 1.76 | 2.55 | 1.45 | 2.01 |
| tryptophan | B-2 | 0.63 | 0.93 | 1.48 | 1.00 |

TABLE 2

Optical resolution of arginine by columns 2 to 6

| column | conditions | retention factor first peak | second peak | separation factor | separation degree |
|---|---|---|---|---|---|
| column 2 | A-1 | 0.30 | 0.93 | 3.09 | 2.88 |
| column 3 | A-1 | 0.35 | 1.15 | 3.29 | 2.89 |
| column 4 | A-1 | 0.38 | 1.24 | 3.24 | 2.94 |
| column 5 | A-1 | 0.37 | 1.03 | 2.77 | 3.10 |
| column 6 | A-1 | 0.32 | 0.85 | 2.66 | 2.27 |

TABLE 3

Optical resolution of tyrosine by columns 2 to 6

| column | conditions | retention factor first peak | second peak | separation factor | separation degree |
|---|---|---|---|---|---|
| column 2 | A-1 | 1.62 | 2.91 | 1.79 | 2.94 |
| column 3 | A-1 | 2.03 | 4.01 | 1.97 | 2.73 |
| column 4 | A-1 | 2.18 | 4.38 | 2.01 | 2.36 |
| column 5 | A-1 | 1.86 | 3.18 | 1.71 | 2.73 |
| column 6 | A-1 | 1.77 | 2.84 | 1.61 | 2.09 |

TABLE 4

Optical resolution with column 4
(aqueous perchloric acid solution/methanol moving phase)

| sample | conditions | retention factor first peak | second peak | separation factor | separation degree |
|---|---|---|---|---|---|
| alanine | B-3 | 0.28 | 1.24 | 4.50 | 3.86 |
| valine | B-5 | 0.52 | 1.47 | 2.82 | 2.16 |
| norvaline | B-3 | 0.41 | 2.18 | 5.38 | 5.58 |
| serine | B-5 | 0.40 | 1.08 | 2.70 | 2.19 |
| threonine | B-3 | 0.08 | 0.33 | 3.85 | 1.10 |
| leucine | B-3 | 0.55 | 3.52 | 6.40 | 6.20 |
| norleucine | B-3 | 0.74 | 3.59 | 4.84 | 6.85 |
| isoleucine | B-3 | 0.26 | 0.95 | 3.67 | 2.95 |
| asparagine | B-5 | 0.47 | 1.10 | 2.34 | 2.07 |
| aspartic acid | B-5 | 1.13 | 3.54 | 3.13 | 3.21 |
| cysteine | B-3 | 0.27 | 0.99 | 3.68 | 3.01 |
| methionine | B-4 | 0.58 | 3.93 | 6.73 | 9.36 |
| glutamic acid | B-3 | 0.30 | 2.44 | 8.07 | 6.31 |
| glutamine | B-3 | 0.12 | 0.87 | 7.15 | 3.42 |
| lysine | B-1 | 1.29 | 2.17 | 1.68 | 1.29 |
| arginine | B-1 | 0.24 | 1.04 | 4.34 | 3.28 |
| histidine | B-5 | 0.61 | 1.64 | 2.70 | 3.27 |
| DOPA | B-4 | 0.40 | 1.67 | 4.14 | 4.82 |
| tyrosine | B-4 | 0.54 | 1.99 | 3.69 | 4.82 |
| phenylglycine | B-4 | 0.67 | 7.21 | 10.69 | 11.66 |
| phenylalanine | B-4 | 0.69 | 2.53 | 3.68 | 5.87 |
| tryptophan | B-4 | 1.79 | 6.28 | 3.51 | 7.58 |
| phenylethylamine | B-4 | 2.50 | 4.10 | 1.64 | 3.86 |
| α-amino-ε-caprolactam | B-3 | 0.20 | 1.03 | 5.19 | 3.77 |

TABLE 5

Optical resolution with column 4
(aqueous perchloric acid solution/acetonitrile moving phase)

| sample | conditions | retention factor first peak | second peak | separation factor | separation degree |
|---|---|---|---|---|---|
| alanine | C-3 | 0.25 | 1.08 | 4.27 | 4.81 |
| valine | C-6 | 0.58 | 2.47 | 4.30 | 6.28 |
| norvaline | C-3 | 0.49 | 2.62 | 5.37 | 9.34 |
| serine | C-6 | 0.35 | 0.93 | 2.64 | 2.74 |
| threonine | A-1 | 0.08 | 0.26 | 3.34 | 1.05 |
| leucine | C-3 | 0.78 | 4.75 | 6.07 | 13.47 |
| norleucine | C-4 | 0.68 | 3.59 | 5.31 | 10.98 |
| isoleucine | C-3 | 0.37 | 1.32 | 3.51 | 4.68 |
| asparagine | C-5 | 0.34 | 0.81 | 2.34 | 1.97 |
| aspartic acid | C-6 | 0.87 | 3.11 | 3.60 | 6.52 |
| cysteine | C-4 | 0.27 | 0.97 | 3.66 | 3.87 |
| methionine | C-4 | 0.55 | 3.82 | 6.93 | 11.89 |
| glutamic acid | C-3 | 0.22 | 1.52 | 6.86 | 6.71 |
| glutamine | C-2 | 0.11 | 0.66 | 5.91 | 3.01 |
| lysine | C-2 | 1.06 | 2.05 | 1.93 | 2.41 |
| arginine | C-1 | 0.37 | 1.26 | 3.37 | 3.53 |
| histidine | C-5 | 0.52 | 1.22 | 2.34 | 3.02 |
| DOPA | C-3 | 0.50 | 1.62 | 3.25 | 5.78 |
| tyrosine | C-3 | 0.77 | 2.50 | 3.23 | 6.90 |
| phenylglycine | C-4 | 0.82 | 9.73 | 11.93 | 19.30 |
| phenylalanine | C-4 | 0.74 | 2.75 | 3.71 | 8.66 |
| tryptophan | C-4 | 1.45 | 5.01 | 3.45 | 11.19 |
| phenylethylamine | C-4 | 4.00 | 6.95 | 1.74 | 7.06 |
| α-amino-ε-caprolactam | C-3 | 0.22 | 1.02 | 4.62 | 5.04 |

TABLE 6

Optical resolution with column 2
(hexane/ethanol moving phase)

| sample | conditions | retention factor first peak | retention factor second peak | separation factor | separation degree |
|---|---|---|---|---|---|
| alanine | D | 1.47 | 6.77 | 4.62 | 8.84 |
| asparagine | D | 1.37 | 2.77 | 2.03 | 2.66 |
| methionine | D | 0.92 | 7.16 | 7.80 | 8.85 |
| arginine | D | 1.08 | 7.29 | 6.75 | 7.92 |
| histidine | D | 0.81 | 1.84 | 2.29 | 2.30 |
| DOPA | D | 0.73 | 4.40 | 6.03 | 5.98 |
| tyrosine | D | 0.49 | 2.85 | 5.88 | 5.87 |
| phenylglycine | D | 0.57 | 6.82 | 11.91 | 8.59 |
| phenylalanine | D | 0.67 | 3.54 | 5.26 | 5.38 |
| tryptophan | D | 1.03 | 5.37 | 5.21 | 5.74 |
| phenylethylamine | D | 1.65 | 2.86 | 1.73 | 2.63 |
| α-amino-ε-caprolactam | D | 0.70 | 3.69 | 5.29 | 6.54 |

INDUSTRIAL APPLICABILITY

The separating agent for chromatography, which contains a binaphthyl derivative and a crown ether-like cyclic structure, makes it possible to adjust the separation characteristics through such factors as, for example, the type of substituent introduced into the binaphthyl and the size of the crown ether-like cyclic structure. Because the present invention enables a more facile synthesis, using about half the steps as in the prior art, of a separating agent for chromatography that has a binaphthyl derivative and a crown ether-like cyclic structure, there are strong expectations that the present invention will enable and support the further elucidation of the separation characteristics of this separating agent and the development of separating agents that exhibit novel separation capabilities.

The invention claimed is:

1. A separating agent for chromatography, having a carrier and an optically active binaphthyl compound bonded by chemical bonding to the surface of the carrier, wherein the binaphthyl compound is represented by the following formula (I):

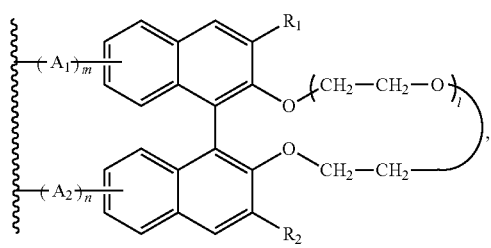

(I)

$R_1$ and $R_2$ each representing a substituted or unsubstituted phenyl group for at least one of a methyl group and a chloro group;

$A_1$ and $A_2$ each representing a group that is bonded to the surface of the carrier and containing a structure represented by the following formula (II) that is substituted for hydrogen in a binaphthyl group of formula (I):

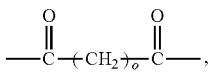

(II)

o representing an integer from 1 to 30; and
l representing an integer from 4 to 6, and m and n each representing an integer from 0 to 5, wherein m+n is from 1 to 10.

2. The separating agent for chromatography according to claim 1, wherein l is 4.

3. The separating agent for chromatography according to claim 1, wherein $R_1$ and $R_2$ are the phenyl group.

4. The separating agent for chromatography according to claim 1, wherein one of m and n is 1 and the other is 0.

5. The separating agent for chromatography according to claim 1, wherein the surface of the carrier exhibits hydrophobicity.

6. A method of producing a separating agent for chromatography, comprising:
a step B of introducing a group containing a structure of the following formula (II) for binding to a carrier into a binaphthyl ring of a binaphthyl group-containing compound A represented by the following formula (III) that is substituted for hydrogen in the binaphthyl group, to obtain a binaphthyl group-containing compound B;
a step C of hydrolyzing methoxy groups at positions 2 and 2' of the binaphthyl group-containing compound B to obtain a binaphthyl group-containing compound C in which the methoxy groups have been converted into hydroxyl groups;
a step D of crosslinking both of the hydroxyl groups in the binaphthyl group-containing compound C with a polyethylene glycol group-containing compound to obtain a binaphthyl group-containing compound D having a crown ether-like cyclic structure; and
a step E of bonding the binaphthyl group-containing compound D to the surface of the carrier through the group for binding to the carrier on the binaphthyl group-containing compound D by chemical bonding,

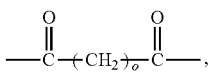

(II)

o representing an integer from 1 to 30; and
l representing an integer from 4 to 6, and m and n each representing an integer from 0 to 5, wherein m+n is from 1 to 10,

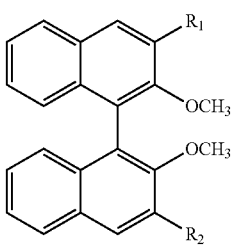

(III)

R$_1$ and R$_2$ each representing hydrogen, a substituted or unsubstituted phenyl group, a substituted or unsubstituted naphthyl group, a substituted or unsubstituted C$_{1-8}$ alkyl group in which any methylene group not adjacent to another methylene group may be oxygen, or a trialkylsilyl group in which the number of carbons in each alkyl group is 1 or 2.

7. The method of producing a separating agent for chromatography according to claim 6, further comprising:

a step A of substituting bromo groups in 3,3'-dibromo-2,2'-dimethoxy-1,1'-binaphthyl with R$_1$ and R$_2$, respectively, to obtain the binaphthyl group-containing compound A.

8. The method of producing a separating agent for chromatography according to claim 6, wherein the binaphthyl group-containing compound B is obtained in step B by reacting the binaphthyl group-containing compound A with a C$_{4-33}$ aliphatic dicarboxylic acid monomethyl ester monochloride in the presence of iron chloride.

9. The method of producing a separating agent for chromatography according to claim 6, wherein the binaphthyl group-containing compound D is obtained in step D by crosslinking the hydroxyl groups in the binaphthyl group-containing compound C by the reaction, under alkaline conditions, of polyoxyethylene glycol ditosylate having from 5 to 7 repetitions of an oxyethylene group.

10. The method of producing a separating agent for chromatography according to claim 6, wherein in step E, a surface-treated silica gel is used for the carrier and chemical bonding is effected between the group for binding to the carrier in the binaphthyl group-containing compound D and a functional group provided by the surface treatment of the silica gel.

11. The method of producing a separating agent for chromatography according to claim 6, further comprising:

a step F of hydrophobing hydrophilic groups on the surface of the carrier.

* * * * *